United States Patent
Miehlich et al.

(10) Patent No.: US 10,092,499 B2
(45) Date of Patent: Oct. 9, 2018

(54) ORAL AND DENTAL CARE AND CLEANING AGENTS COMPRISING PHOSPHATE-CONTAINING AND/OR PHOSPHONATE-CONTAINING POLYURETHANE POLYMERS

(71) Applicant: Henkel AG & Co. KGaA, Duesseldorf (DE)

(72) Inventors: Kristin Miehlich, Wuppertal (DE); Daniela Arians, Essen (DE); Andreas Taden, Duesseldorf (DE); Detlef Buisker, Essen (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/377,530

(22) Filed: Dec. 13, 2016

(65) Prior Publication Data
US 2017/0165189 A1 Jun. 15, 2017

(30) Foreign Application Priority Data
Dec. 14, 2015 (DE) .......................... 10 2015 225 140

(51) Int. Cl.
| | | |
|---|---|---|
| *A61K 8/87* | (2006.01) | |
| *A61Q 11/00* | (2006.01) | |
| *A61K 8/86* | (2006.01) | |
| *A61K 8/85* | (2006.01) | |
| *A61K 8/46* | (2006.01) | |
| *A46B 9/04* | (2006.01) | |
| *A61C 17/22* | (2006.01) | |

(52) U.S. Cl.
CPC ................ *A61K 8/87* (2013.01); *A46B 9/04* (2013.01); *A61C 17/22* (2013.01); *A61K 8/463* (2013.01); *A61K 8/85* (2013.01); *A61K 8/86* (2013.01); *A61Q 11/00* (2013.01); *A61K 2800/5422* (2013.01); *A61K 2800/594* (2013.01)

(58) Field of Classification Search
None
See application file for complete search history.

(56) References Cited

U.S. PATENT DOCUMENTS

| | | | | |
|---|---|---|---|---|
| 2004/0197293 A1* | 10/2004 | Mougin | ............... | A61K 8/87 424/70.17 |
| 2004/0241104 A1* | 12/2004 | Le Bourhis | ............ | A61K 8/046 424/47 |
| 2013/0289201 A1* | 10/2013 | Berge | ..................... | C09D 11/30 524/591 |

OTHER PUBLICATIONS

DIN 53 601 "Determination of the Dibutylphthalate Absorption of Carbon Blacks", 1978.
DIN 53240-2 "Determination of Hydroxyl Value—Part 2: Method with Catalyse", 2007.

* cited by examiner

Primary Examiner — Brian Gulledge
(74) Attorney, Agent, or Firm — P. Scott Smith

(57) ABSTRACT

The present invention relates to oral and dental care and cleaning agents comprising an aqueous dispersion of a phosphate-containing and/or phosphonate-containing polyurethane polymer and anionic surfactant(s), to tooth cleaning methods using these agents, and to the use of oral and dental care and cleaning agents comprising an aqueous dispersion of a phosphate-containing and/or phosphonate-containing polyurethane polymer and anionic surfactant(s) to reduce the restaining of teeth and/or to reduce biofilm development on dental surfaces and/or to reduce the adhesion of bacteria to dental surfaces and/or to extend the antibacterial action of antibacterial substances.

19 Claims, No Drawings

ORAL AND DENTAL CARE AND CLEANING AGENTS COMPRISING PHOSPHATE-CONTAINING AND/OR PHOSPHONATE-CONTAINING POLYURETHANE POLYMERS

FIELD OF THE INVENTION

The present invention generally relates to oral and dental care and cleaning agents comprising an aqueous dispersion of a phosphate-containing and/or phosphonate-containing polyurethane polymer and anionic surfactant(s). Such agents result in reduced restaining of the teeth from foodstuffs and bacterial impurities after brushing the teeth.

The present invention further relates to a method for cleaning teeth using the agent according to the invention.

Finally, the present invention relates to the use of oral and dental care and cleaning agents comprising an aqueous dispersion of a phosphate-containing and/or phosphonate-containing polyurethane polymer and anionic surfactant(s) to reduce the restaining of teeth and/or to reduce biofilm development on dental surfaces and/or to reduce the adhesion of bacteria to dental surfaces and/or to extend the antibacterial action of antibacterial substances.

BACKGROUND OF THE INVENTION

Dental care products and dental cleaning products are available on the market in various forms and are used primarily to clean the surface of the teeth and prevent tooth and periodontal diseases. They usually include a combination of polishing agents, humectants, surfactants, binding agents, flavoring agents, and fluoride-containing and antimicrobial active substances. In addition to tooth powders, which, due to the increased abrasiveness thereof, play a lesser role, dental cleaning products are offered above all in paste, cream and translucent or transparent gel forms. In recent years, liquid toothpastes and mouthwashes have also increasingly gained in importance.

Many consumers perceive dark or stained teeth to be cosmetically unacceptable. Despite regular dental hygiene, attempts to preserve the natural tooth color are not always successful. Dietary habits or smoking can result in discoloration of the teeth. Likewise, the colonization of the tooth surface by bacteria (plaque) leads to discoloration.

A number of technical solutions for stain removal or whitening of teeth were therefore developed in the prior art. Peroxide is used primarily for whitening/bleaching. Peroxide is used in high concentrations in professional bleaching products, whereas the use in cosmetic products for oral and dental care is limited to 0.1% peroxide. At this concentration, however, peroxide has only limited whitening action and often does not eliminate tooth discoloration to the desired extent.

Another option for whitening teeth is the effective removal of plaque, which makes teeth appear darker. This method of tooth whitening is also described as "natural whitening." A high cleaning performance is achieved by the use of abrasives, such as silica, alumina, or calcium carbonate, in combination with a surfactant. Unfortunately, toothpastes comprising an effective system of one or more these cleaning and polishing agents often also have a high abrasiveness, and therefore often lead to abrasion of the tooth surface. This can be disadvantageous in particular when the tooth enamel is already thin, as is the case in people with sensitive teeth. Exposed tooth necks also occur often in individuals with sensitive teeth, which is to say the portions of the tooth in the immediate vicinity of the gingiva where no enamel is present as a protective layer and the dentin underneath is exposed. The above-described individuals are thus not able to use such dental cleaning agents, or use these only to a very limited extent.

Moreover, immediately after cleaning the teeth, a protein layer (pellicle) forms on the tooth material, on which plaque builds up or discolorations accumulate.

A need therefore exists for oral and dental care and cleaning agents that result in effective cleaning and whitening of the teeth, while also preventing the formation of new discolorations for as long as possible. At the same time, an antibacterial action that lasts as long as possible was to be achieved.

The object of the present invention was therefore to provide oral and dental care and cleaning agents that prevent or reduce new discolorations of the teeth for as long as possible after the teeth have been cleaned. Furthermore, these agents are to have a high cleaning performance and result in an effective reduction of plaque. In addition, these agents are to have a long shelf life.

Surprisingly, it was found that the use of an aqueous dispersion of phosphate-containing and/or phosphonate-containing polyurethanes, in combination with anionic surfactant(s), results in reduced restaining of the teeth from foods (such as tea) and bacterial impurities. Moreover, the use of the above-mentioned combination does not adversely affect the cleaning action and the reduction of plaque.

Furthermore, other desirable features and characteristics of the present invention will become apparent from the subsequent detailed description of the invention and the appended claims, taken in conjunction with this background of the invention.

BRIEF SUMMARY OF THE INVENTION

An oral and dental care and cleaning agent, comprising, based on the total weight thereof, 1 to 20 wt. % of an aqueous dispersion of at least one phosphate-containing and/or phosphonate-containing polyurethane polymer, and 0.5 to 40 wt. % anionic surfactant(s).

Use of oral and dental care and cleaning agents, comprising, based on the weight thereof, 1 to 20 wt. % of an aqueous dispersion of at least one phosphate-containing and/or phosphonate-containing polyurethane polymer, and 0.5 to 40 wt. % anionic surfactant(s) to reduce the restaining of teeth and/or to reduce biofilm development on dental surfaces and/or to reduce the adhesion of bacteria to dental surfaces and/or to extend the antibacterial action of antibacterial substances.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject matter of the present invention is an oral and dental care and cleaning agent, comprising, based on the total weight thereof,
a) 1 to 20 wt. % of an aqueous dispersion of at least one phosphate-containing and/or phosphonate-containing polyurethane polymer, and
b) 0.5 to 40 wt. % anionic surfactant(s).

The phosphate-containing and/or phosphonate-containing polyurethane polymer exhibits a high absorption rate on hydroxylapatite, and thus on tooth enamel, 95% of which is made of hydroxylapatite. In this way, the use of an aqueous dispersion of this polyurethane polymer in oral and dental care or cleaning agents during care or cleaning allows this polymer to be deposited onto the tooth enamel. The deposition of the phosphate-containing and/or phosphonate-containing polyurethane polymer on the tooth enamel reduces or prevents restaining of the teeth, for example due to bacterial impurities or foodstuff ingredients, such as tea. Moreover, the aqueous dispersions of these polyurethane polymers have a high compatibility with anionic surfactants, so that these dispersions can be readily incorporated into existing formulations, without reducing the shelf life of these products.

Oral and dental care products and oral and dental cleaning products within the meaning of the invention are oral and tooth powders, oral pastes and toothpastes, liquid oral creams and dentifrices, oral and dental rinses, and oral and dental gels. Toothpastes and liquid dental cleaning products are preferably suited. For this purpose, the oral and dental care and cleaning agents may be present, for example, in the form of toothpastes, liquid dentifrices, tooth powders, mouthwashes or optionally also as a chewing compound, such as chewing gum. It is preferred, however, if these are present as substantially flowable or plastic toothpastes, as they are used to clean teeth along with a toothbrush. A further particularly preferred embodiment of the present invention is oral rinse solutions and mouthwashes that are used to rinse out the oral cavity.

The term "polyurethane polymer" within the scope of the present invention shall be understood to mean polymers in which the particular monomer units are linked by urethane groupings of the general formula —NH—CO—O—. Polyurethane polymers used according to the invention are preferably obtained by polyaddition from dihydric or polyhydric alcohols with diisocyanates and/or triisocyanates.

Furthermore, the term "phosphate-containing and/or phosphonate-containing polyurethane polymer" shall be understood to mean polyurethane polymers that comprise at least one covalently bound phosphate —O—$PO_3^{2-}$ and/or at least one covalently bound phosphonate group —$PO_3^{2-}$. The covalent binding of these groups can be achieved by using compounds that, in addition to the phosphate group or phosphonate group, also comprise a nucleophilic group, such as an OH— or $NH_2$— group. These nucleophilic groups react with free isocyanate groups of the polyurethane polymer, or polyurethane prepolymer, forming covalent bonds.

Within the scope of the present invention, the term "aqueous dispersions" shall be understood to mean multiphase compositions that comprise a continuously aqueous phase and a phase of at least one phosphate-containing and/or phosphonate-containing polyurethane polymer which is finely distributed in this aqueous phase.

According to the invention, the term "anionic surfactant" shall be understood to mean amphiphilic (bifunctional) compounds that are composed of at least one hydrophobic molecule part and at least one hydrophilic molecule part. The hydrophobic group is preferably a hydrocarbon chain having 8 to 28 carbon atoms, which can be saturated or unsaturated, linear or branched. This $C_8$ to $C_{28}$ alkyl chain is particularly preferably linear. Furthermore, these surfactants comprise at least one carboxylate group and/or sulfonate group.

Moreover, the term "fatty acid", as it is used within the scope of the present invention, shall be understood to mean aliphatic carboxylic acids that include unbranched or branched carbon groups having 4 to 40 carbon atoms. The fatty acids used within the scope of the present invention can be both naturally occurring and synthetically produced fatty acids. The fatty acids can moreover be monounsaturated or polyunsaturated.

Finally, the term "fatty alcohol" within the scope of the present invention shall be understood to mean aliphatic, monohydric, primary alcohols that include unbranched or branched hydrocarbon groups having 4 to 40 carbon atoms. The fatty alcohols used within the scope of the invention can also be monounsaturated or polyunsaturated.

As a first essential component a), the compositions according to the invention comprise at least one aqueous dispersion at least one phosphate-containing and/or phosphonate-containing polyurethane polymer.

The phosphate-containing and/or phosphonate-containing polyurethane polymer used according to the invention preferably includes certain structural units. Preferred embodiments of the cosmetic agents according to the invention are thus characterized in that the at least one phosphate-containing and/or phosphonate-containing polyurethane polymer comprises at least one polyurethane compound of formula (I), and at least one ionic polyether compound of formula (II), and at least one non-ionic polyether compound of formula (III), and at least one phosphate-containing and/or phosphonate-containing compound of formula (IVa) and/or (IVb) and/or (IVc)

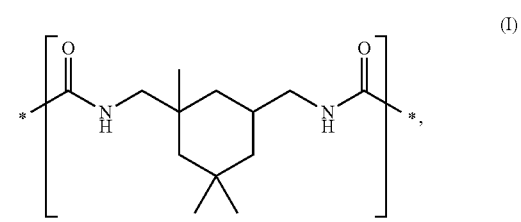

(I)

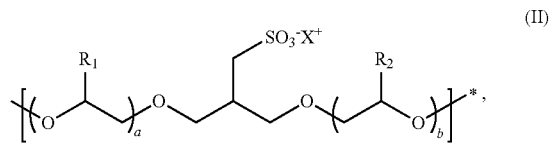

(II)

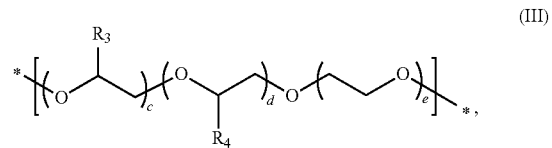

(III)

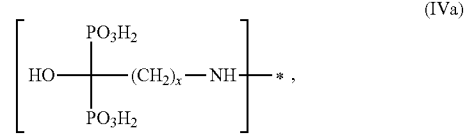

(IVa)

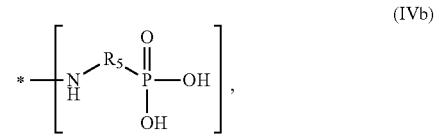

(IVb)

$$\ast-\left[-O^{R_5}\underset{OH}{\overset{O}{\underset{\|}{P}}}-OH\right], \quad (IVc)$$

where
- $R_1$ and $R_2$, each independently of one another, denote a linear or branched $C_1$ to $C_4$ alkyl group, in particular a linear $C_1$ to $C_2$ alkyl group; a and b, each independently of one another, denote integers from 1 to 6, in particular from 1 to 4; $X^+$ denotes a physiologically compatible cation, in particular sodium;
- $R_3$ and $R_4$, each independently of one another, denote hydrogen or a linear or branched $C_1$ to $C_4$ alkyl group, in particular hydrogen or a linear $C_1$ to $C_2$ alkyl group, wherein at least one of the groups $R_3$ or $R_4$ denotes a linear or branched $C_1$ to $C_4$ alkyl group; e denotes integers from 1 to 15, preferably from 1 to 7; and c and d, each independently of one another, denote integers from 10 to 60, preferably from 20 to 40;
- x denotes integers from 1 to 10, preferably from 2 to 8; and
- $R_5$ denotes a respective linear or branched $C_1$ to $C_4$ alkyl group, in particular a linear $C_1$ to $C_2$ alkyl group.

Polyurethane compounds shall be understood to mean compounds that comprise at least two urethane groups —NH—C(O)—. Furthermore, polyether compounds shall be understood to mean compounds that comprise at least two ether groups. Ionic polyether compounds comprise at least one group having a cationic charge and/or an anionic charge, preferably an anionic charge, in particular at least one sulfonate group —$SO_3^-$, while non-ionic polyether compounds have no charged groups whatsoever, regardless of the pH value. The polyurethane polymers can be produced, for example, by reacting polyisocyanates (compound having at least two isocyanate groups) with polyols (compound having at least two free OH groups), diols and amines. However, it is preferred within the scope of the present invention if initially an NCO group-terminated polyurethane prepolymer is produced by reacting an excess of a diisocyanate, for example a diisocyanate corresponding to formula (I), with an ionic polyether polyol corresponding to formula (II) and a non-ionic polyether polyol corresponding to formula (III). This polyurethane prepolymer is then reacted with a phosphate-containing and/or phosphonate-containing compound corresponding to one of formulas (IVa) and/or (IVb) and/or (IVc), wherein the free OH or $NH_2$ group of the phosphate-containing and/or phosphonate-containing compound reacts with the at least one free NCO group of the polyurethane polymer, forming a covalent bond. By functionalizing the polyurethane polymer with phosphates and/or phosphonates, effective deposition of these polymers on the tooth enamel is achieved. This reduces or prevents the restaining of teeth from bacterial impurities or foodstuffs.

According to the above formulas and all formulas provided hereafter, a chemical bond identified by the "*" symbol denotes a free valence of the corresponding structure fragment. Free valence here shall be understood to mean the number of atom bonds originating from the corresponding structure fragment at the position identified with the "c*" symbol. Within the scope of the present invention, preferably a respective atomic bond extends from the positions of the structure fragments identified by the "*" symbol to further structural fragments.

Furthermore, it may be preferred within the scope of the present invention in this context if the polyurethane polymer comprises certain ionic polyether compounds of formula (II) and certain non-ionic polyether compounds of formula (III). Preferred agents of the present invention are thus characterized in that the at least one phosphate-containing and/or phosphonate-containing polyurethane polymer comprises at least one ionic polyether compound of formula (IIa)

$$\ast{\left[{O\sim}\right]_a} O\sim\underset{\overset{|}{SO_3^-X^+}}{}\sim O{\left[\sim O\right]_b}\ast \quad (II)$$

where
a and b, each independently of one another, denote integers from 1 to 4, and $X^+$ denotes sodium. The use of sulfonate-containing polyether compounds of formula (IIa) has proven to be particularly advantageous with respect to the stability of the polyurethane polymer in the aqueous dispersion, so that the shelf life of the agents can be improved by the use of these polyether compounds.

Furthermore, it is preferred within the scope of the present invention if the at least one phosphate-containing and/or phosphonate-containing polyurethane polymer comprises at least one non-ionic polyether compound of formula (IIIa)

$$\ast{\left[{O\sim}\right]_c}{\left[O\sim\right]_d}O{\left[\sim O\right]_e}\ast, \quad (IIIa)$$

where
c and e, each independently of one another, denote integers from 1 to 7; and d denotes integers from 20 to 40. Due to the additional use of the above-described polyether compounds of formula (IIIa), the phosphate-containing and/or phosphonate-containing polyurethane polymer can be further stabilized. Moreover, the use of these polyether compounds has proven to be advantageous with respect to the particle size distribution of the polyurethane polymers since the use of these non-ionic polyether compounds allows a narrower particle size distribution to be achieved. The non-ionic polyether compounds of formula (IIIa) are preferably ethylene oxide-propylene oxide block copolymers, which have only a small content of ethylene oxide.

The non-ionic polyether compound of formula (III), and in particular of formula (IIIa), preferably has certain number average molecular weights $M_n$. The number average molecular weight $M_n$ is ascertained by determining the hydroxyl number in accordance with DIN 53240-2 (November 2007). It is preferred in this context if the at least one non-ionic polyether compound of formula (III), and in particular of formula (IIIa), has a number average molecular weight $M_n$ of 500 to 5,000 g/mol, especially of 800 to 4,000/gmol, preferably of 1,000 to 3,000 g/mol, and in particular of 1,800 to 2,200 g/mol.

Moreover, it has proven advantageous if the phosphate-containing and/or phosphonate-containing polyurethane polymer comprises at least two non-ionic polyether compounds of formula (III), and in particular (IIIa), which have different number average molecular weights $M_n$, in a certain weight ratio (based on the total weight of this mixture). The number average molecular weights $M_n$ of these two non-ionic polyether compounds are preferably within the above-described number average molecular weights. It is thus advantageous if the at least one phosphate-containing and/or phosphonate-containing polyurethane polymer comprises at least two non-ionic polyether compounds, each having the formula (III), and in particular (IIIa), and having number average molecular weights $M_n$ that are different from one another, in a weight ratio of 1:1. The use of two different polyether compounds of formula (III), and in particular of formula (IIIa), allows the stability of the polyurethane polymer particles in the aqueous dispersion to be further increased. Furthermore, the use of the above-described mixture of the two polyether compounds of formula (III), and in particular of formula (IIIa), has proven to be advantageous with respect to a narrower particle size distribution of the phosphate-containing and/or phosphonate-containing polyurethane polymer.

The use of certain phosphonate-containing compounds has proven to be particularly advantageous within the scope of the present invention. It is therefore advantageous according to the invention to use aqueous dispersions of phosphonate-containing polyurethane polymers. Preferred embodiments of the present invention are thus characterized in that the at least one phosphate-containing and/or phosphonate-containing polyurethane polymer comprises at least one phosphonate-containing compound of formula (IVa-1) and/or (IVb-1) and/or (IVc-1)

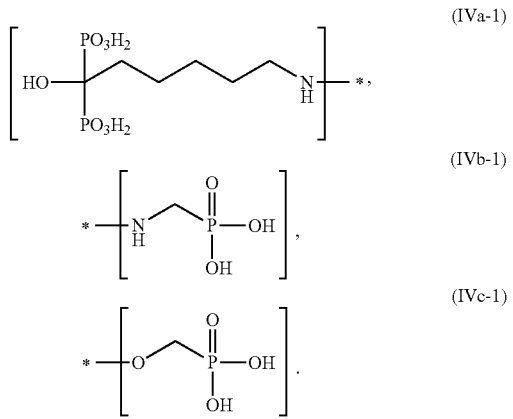

The compound corresponding to formula (IVa-1) is also referred to as (6-amino-1-hydroxyhexane-1,1-diyl)bis(phosphonic acid) (CAS number 79778-41-9) and is also known by the name of neridronic acid. Formula (IVb-1) corresponds to the compound aminomethylphosphonic acid (CAS number: 1066-51-9), and formula (IVc-1) to the compound hydroxymethylphosphonic acid (CAS number: 2617-47-2). The use of these phosphonate-containing compounds has proven to be particularly advantageous with respect to the deposition of the phosphonate-containing polyurethane polymer on the tooth enamel, and thus the prevention or reduction of restaining.

The phosphate-containing and/or phosphonate-containing polyurethane polymer of the present invention preferably comprises the at least one polyurethane compound of formula (I), which corresponds to the polyisocyanate that is used, in certain weight proportions. Preferred embodiments of the present invention are thus characterized in that the at least one phosphate-containing and/or phosphonate-containing polyurethane polymer comprises the at least one polyurethane compound of formula (I), based on the total weight thereof, in a total amount of 4.0 to 30 wt. %, especially of 5.0 to 25 wt. %, preferably of 8.0 to 20 wt. %, and in particular of 10 to 15 wt. %.

The use of a certain weight ratio of the at least one ionic polyether compound of formula (II), and in particular (IIa), to the at least one non-ionic polyether compound of formula (III), and in particular (IIIa), can be advantageous according to the invention. It is thus preferred if the at least one phosphate-containing and/or phosphonate-containing polyurethane polymer has a weight ratio of the at least one ionic polyether compound of formula (II), and in particular of formula (IIa), to the at least one non-ionic polyether compound of formula (III), and in particular of formula (IIIa), of 2:1 to 1:5, especially of 2:1 to 1:3, and in particular of 2:1 to 1:2. The use of such a weight ratio of the ionic polyether compound of formula (II), and in particular of formula (IIa), to the non-ionic polyether compound of formula (III), and in particular of formula (IIIa), has proven to be particularly advantageous for the stability of the phosphate-containing and/or phosphonate-containing polyurethane polymers in the aqueous dispersion. Without intending to be bound to this theory, the use of the above-described weight ratios inhibits crystallization within the polyurethane polymer, resulting in a reduced formation of crystallites, which are responsible for the decreased stability of the polyurethane polymer in the aqueous dispersion.

Moreover, it is advantageous within the scope of the present invention if the at least one ionic polyether compound of formula (II), and in particular of formula (IIa), and the at least one non-ionic polyether compound of formula (III), and in particular of formula (IIIa), are present in certain weight proportions in the polyurethane polymer. Preferred embodiments of the present invention are thus characterized in that the at least one phosphate-containing and/or phosphonate-containing polyurethane polymer comprises the at least one ionic polyether compound of formula (II), and in particular of formula (IIa), based on the total weight thereof, in a total amount of 2.0 to 7.0 wt. %, especially of 2.5 to 6.0 wt. %, preferably of 3.0 to 5.0 wt. %, and in particular of 3.5 to 4.5 wt. %.

Moreover, it has proven advantageous according to the invention if the at least one phosphate-containing and/or phosphonate-containing polyurethane polymer comprises the at least one non-ionic polyether compound of formula (III), and in particular of formula (IIIa), based on the total weight thereof, in a total amount of 4.0 to 20 wt. %, especially of 5.0 to 15 wt. %, preferably of 6.0 to 12 wt. %, and in particular of 7.5 to 9.5 wt. %.

According to the invention, the phosphate-containing and/or phosphonate-containing polyurethane polymer additionally preferably comprises at least one polyester compound. According to the invention, polyester compounds shall be understood to mean compounds that comprise at least two ester groups and can be obtained, for example, by reacting a carboxylic acid with an excess of alcohol. Preferred embodiments are thus characterized in that the at least one phosphate-containing and/or phosphonate-containing polyurethane polymer additionally comprises at least one polyester compound, selected from condensates of adipic acid with butylene glycol, condensates of azelaic acid with 1,6-hexanediol, and the mixtures thereof. These polyester compounds are preferably crystalline or semi-crystalline and have a melting point $T_m$ of >40° C. to <160° C. The melting point information refers to the melting point of corresponding high-molecular-weight linear polyester homopolymers. Methods suitable for determining the enthalpy of fusion, the melting points, and the crystallinity are known in the prior art and well-established. In particular, the determination by way of differential scanning calorimetry (DSC) in accordance with ISO 11357 at a heating rate of 20 K/min is suitable, wherein the results of the second heating run are to be used to determine the enthalpy of fusion. Moreover, the above-described polyester compounds preferably have enthalpies of fusion above 90 J/g, and in particular above 115 J/g. "Crystalline," as used in the present context, refers to a crystallinity of at least 90%, and preferably at least 95%. Similarly, "semi-crystalline," as used herein, means that the corresponding polyester compounds have a crystallinity of at least 50%, and especially at least 70%, but less than 90%. Semi-crystalline polyester compounds thus comprise crystalline and non-crystalline, which is to say amorphous, regions.

Polyurethane polymers of this embodiment thus comprise crystalline segments and thus have a crystallinity of at least 20%, especially of at least 35%, and in particular of at least 50%. The crystallinity can be determined, for example, by way of dynamic scanning calorimetry (DSC) in accordance with ISO 11357-3 (2013) at a heating rate of 10 K/min. The polyurethane prepolymers are preferably reacted with a suitable reagent for this purpose, such as dibutylamine. Since the crystallinity depends on the temperature history of the corresponding polymer, it is preferred according to the invention to store the polyurethane polymers for at least 24 hours, and in particular for at least one week, at a temperature of 5 kelvin below the melting point thereof (determined by way of DSC in accordance with ISO 11357-3).

In this context, it has proven advantageous if the polyester compound has a certain number average molecular weight $M_n$. The number average molecular weight $M_n$ is ascertained by determining the hydroxyl number in accordance with DIN 53240-2 (November 2007). It is thus preferred in this context if the at least one polyester compound has a number average molecular weight $M_n$ of 1,200 to 5,500 g/mol, especially of 1,500 to 5,000/gmol, preferably of 1,800 to 4,500 g/mol, and in particular of 2,000 to 4,000 g/mol.

Moreover, it may be preferred in this context if the phosphate-containing and/or phosphonate-containing polyurethane polymer comprises a certain weight proportion of the polyester compound. Preferred embodiments are thus characterized in that the at least one phosphate-containing and/or phosphonate-containing polyurethane polymer comprises the at least one polyester compound, based on the total weight thereof, in a total amount of 55 to 87 wt. %, especially of 60 to 85 wt. %, preferably of 65 to 82 wt. %, and in particular of 70 to 80 wt. %. The use of polyester compounds in the above-described weight proportions has proven to be advantageous with respect to the stability of the phosphate-containing and/or phosphonate-containing polyurethane polymers in the aqueous dispersion.

It may furthermore be provided that the phosphate-containing and/or phosphonate-containing polyurethane polymer additionally comprises silicone-containing polyether compounds, for example in the form of dihydroxyalkyl polydimethylsiloxane of formula (IV)

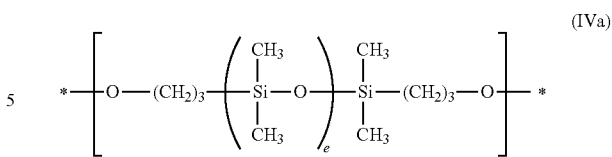

where
e denotes integers from 25 to 45. These polyether compounds can be present in the phosphate-containing and/or phosphonate-containing polyurethane polymer instead of or together with the above-described polyether compounds. The silicone-containing polyether compounds of formula (IV) can be present in a total amount of 10 to 80 wt. %, especially 12 to 75 wt. %, preferably 15 to 72 wt. %, and in particular 18 to 72 wt. %, based on the total weight of the polyurethane polymer.

The phosphate-containing and/or phosphonate-containing polyurethane polymer can additionally comprise low-molecular-weight diol and/or diamine compounds as chain extenders. For example, such compounds are selected from the group consisting of 1,2-propanediol, 1,3-propanediol, 1,4-butanediol, neopentyl glycol, 1,6-hexanediol, hydrazine, polyether diamines, alkylene diamines, cycloalkylene diamines, isophorone diamine, piperazine, neopentyl diamine, and the mixtures thereof. If such diol and/or diamine compounds are used, these are preferably present in a total amount of 0.1 to 10 wt. %, especially 0.2 to 5.0 wt. %, preferably 0.3 to 3.0 wt. %, and in particular 0.5 to 1.5 wt. %, based on the total weight of the polyurethane polymer.

The phosphate-containing and/or phosphonate-containing polyurethane polymers can be obtained by mixing the polyisocyanate corresponding to the polyurethane compound of formula (I) with the polyether polyols corresponding to the polyether compounds of formulas (II) and (III) or (IIa) and (IIIa), and the phosphate-containing and/or phosphonate-containing compound corresponding to formulas (IVa) to (IVc), or (IVa-1) to (IVc-1), and optionally the further above-described polyester compounds, silicone-containing polyether compounds, diols and diamines, adding a catalyst. However, it is preferred within the scope of the present invention if initially NCO group-terminated polyurethane prepolymers are produced by adding an excess of polyisocyanate, and in particular isophorone diisocyanate (IPDI), to the polyether polyols corresponding to the polyether compounds of formulas (II) and (III) or (IIa) and (IIIa), and optionally the further polyester compound, silicone-containing polyether compound and diols, using a catalyst, at elevated temperatures. The polyether polyols corresponding to the polyether compounds of formulas (II) and (III) or (IIa) and (IIIa), and optionally the further polyester compounds and polyether compounds, are preferably heated to temperatures of 70 to 95° C., and in particular 75° C., to melt these compounds. It may furthermore be preferred to stir this molten mixture under vacuum so as to dry it. If a diol is used, this is preferably added to the mixture after drying. The at least one polyisocyanate is preferably added at temperatures of 50 to 65° C., and in particular 60° C. The polyurethane prepolymer is preferably formed at temperatures of 70 to 95° C., and in particular 80° C., for a period of 1 to 24 hours. To accelerate the formation of the polyurethane prepolymer, it may be preferred if at least one catalyst is added to the mixture of polyols and the at least one polyisocyanate. Suitable catalysts are tin-, bismuth- or zinc-based, for example. A particularly preferably used catalyst is dimethyltin dineodecanoate, which is available from Momentive Performance Materials GmbH (Germany) under the trade name Fomrez UL28. Furthermore, the use of bismuth neodecanoate and tin neodecanoate is preferred, which are available from OMG Borchers GmbH (Germany) under the trade names BorchiKat 315 and BorchiKat 0716 is preferred.

The formation of the polyurethane prepolymer is interrupted when the content of free isocyanate groups has reached the calculated number. The content of free isocyanate groups can be ascertained, for example, by way of standard titration with dibutylamine in accordance with EN ISO 11909:2007-05. Preferred contents of free isocyanate in the polyurethane prepolymer are 0.2 to 3.0 wt. %, and in particular 1.0 to 2.0 wt. %, based on the total amount of polyols and polyisocyanates.

As described above, the polyisocyanate is used in a concentration that is higher than the stoichiometrically required concentration for the polyisocyanate to react completely with all available OH groups of the polyols. The amount of polyisocyanate is preferably 20 to 150% of the stoichiometric amount required for a complete reaction with all OH groups of all polyols used.

As soon as the content of free isocyanate groups has reached the previously defined preferred number, it is preferred to lower the temperature to 40° C., and to dissolve the formed NCO group-terminated polyurethane prepolymer in a suitable organic solvent, such as ethyl acetate or acetone.

It may be preferred within the scope of the present invention to neutralize these ionic groups of the polyurethane prepolymer prior to dispersing the prepolymer. Suitable neutralizing agents are triethylamine, for example.

The aqueous dispersion of the at least one phosphate-containing and/or phosphonate-containing polyurethane polymer can be obtained, for example, by dispersing the polyurethane prepolymer present in the organic solvent in a continuous phase, and then adding the phosphate-containing and/or phosphonate-containing compound, and increasing the pH value to 11 to 12. The continuous phase preferably comprises at least 50 vol %, especially at least 80 vol %, preferably at least 90 vol %, and particularly preferably 100 vol % water, based on the total volume of the continuous phase, as the solvent. Further substances, such as salts and buffers, may be present in this aqueous continuous phase. The dispersion of the prepolymer can take place with vigorous stirring. The dispersion is advantageously carried out at a temperature of 20 to 60° C., and in particular at 40° C. It is possible within the scope of the present invention to achieve the dispersion by mechanical stirring or by the use of dispersing machines, such as high pressure homogenizers, microfluidizers or rotor/stator dispersing machines. The dissolved polyurethane prepolymer is particularly preferably dispersed into a continuous aqueous phase, and in particular water, and the formed pre-dispersion is homogenized so as to form a stable dispersion. According to the invention, the term "dispersion" shall be understood to mean oil-in-water dispersions, or (O/W) dispersions, in which water forms the continuous phase in which the polyurethane prepolymer, or the phosphate-containing and/or phosphonate-containing polyurethane polymer, is dispersed. The homogenization of the pre-dispersion can take place by shear forces, for example by way of a high pressure homogenizer. The homogenizer preferably has an energy input of $10^3$ to $10^5$ J per second per liter of the dispersion. Preferably, shear rates of at least 1,000,000 per second are used. After the dispersion has been carried out, it is preferred to use the at least one phosphate-containing and/or phosphonate-containing compound in a stoichiometric ratio of the free NCO groups of the prepolymer to this compound of 1:1 to 4:1 to achieve a functionalization of the prepolymer with phosphate groups and/or phosphonate groups. This can take place, for example, by adding the corresponding phosphate-containing and/or phosphonate-containing compound to the dispersion of the prepolymer and stirring this dispersion for 10 minutes to 3 hours. Thereafter, it is advantageous to remove the organic solvent, such as ethyl acetate and/or acetone, for example by using a rotary evaporator, so as to further increase the stability of the dispersion.

So as to achieve sufficient adhesion of the phosphate-containing and/or phosphonate-containing polyurethane polymer on the tooth enamel and thus prevent or reduce restaining of the teeth, it is preferred if these polyurethane polymers have certain phosphate contents. Preferred embodiments of the present invention are thus characterized in that the phosphate-containing and/or phosphonate-containing polyurethane polymer has a phosphate content, based on the total weight thereof, of 0.005 to 3.0 wt. %, especially of 0.01 to 2.5 wt. %, preferably of 0.05 to 2.0 wt. %, and in particular of 0.1 to 1.0 wt. %. Such phosphate contents of the polyurethane polymer have proven to be particularly preferred with respect to the adhesion of the polymer on the tooth enamel and the reduction or prevention of the restaining of teeth from bacterial impurities or foodstuffs. The phosphate content is determined by way of ICP-OES. For this purpose, a high pressure incinerator and an ICP spectrometer are used. Initially, 4 mL $HNO_3$ and 0.2 mL $H_2SO_4$ are added to a vessel containing 0.2 to 0.4 g of the freeze-dried dispersion. The vessel is closed tightly and placed in the high pressure incinerator in a nitrogen atmosphere. The temperature is isobarically increased from 25° C. at 100 bar to 80° C. and is then increased for a period of 120 minutes at a maximum pressure of 130 bar to 300° C. This temperature is maintained for 30 minutes, and then cooling to room temperature with ventilation is carried out. This sample is then measured by way of an ICP spectrometer.

It has been found to be advantageous according to the invention if the aqueous dispersion of the at least one phosphate-containing and/or phosphonate-containing polyurethane polymer has a certain volume median particle size D50. It is thus preferred within the scope of the present invention if the aqueous dispersion has a volume median particle size $D_{50}$ of 50 to 500 nm, especially of 80 to 400 nm, preferably of 100 to 400 nm, and in particular 150 to 400 nm. The volume median particle size D50 of the aqueous dispersion is determined by way of dynamic light scattering (DLS) at a solids content of 0.01 wt. %, based on the total weight of the dispersion.

The aqueous dispersion preferably has a certain content of phosphate-containing and/or phosphonate-containing polyurethane polymer. Preferred embodiments according to the invention are thus characterized in that the aqueous dispersion has a solids content, based on the total weight of the dispersion, of 10 to 60 wt. %, especially of 15 to 55 wt. %, preferably of 10 to 52 wt. %, and in particular of 10 to 50 wt. %. The use of aqueous dispersions having the above-described solids contents of the at least one phosphate-containing and/or phosphonate-containing polyurethane polymer reduces the restaining of teeth particularly well.

In addition to the phosphate-containing and/or phosphonate-containing polyurethane polymer, the aqueous dispersion preferably does not include any unbound phosphate-containing and/or phosphonate-containing compounds.

According to the invention, the term "unbound phosphate-containing and/or phosphonate-containing compounds" shall be understood to mean phosphate-containing and/or phosphonate-containing compounds that not are covalently bound to the polyurethane polymer, in particular by reacting a nucleophilic group of the at least one phosphate-containing and/or phosphonate-containing compounds with at least one free NCO group of the at least one polyurethane prepolymer or polyisocyanate. It is thus preferred within the scope of the present invention if the aqueous dispersion does not comprise any unbound phosphate-containing and/or phosphonate-containing compound(s), and in particular phosphate-containing and/or phosphonate-containing compound(s) of formula (IVa) to (IVc), and (IVa-1) to (IVc-1). Unbound phosphate-containing and/or phosphonate-containing compounds can be removed by dialysis of the aqueous dispersion, for example. According to the invention, dialysis membranes made of cellulose esters having a molecular weight cut-off (also referred to as MWCO) of 30,000 Da are preferably used. The dialysis is advantageously carried out against distilled water.

The oral and dental care and cleaning agent preferably comprises the at least one aqueous dispersion of the at least one phosphate-containing and/or phosphonate-containing polyurethane polymer in certain quantity ranges. It is thus advantageous within the scope of the present invention if the oral and dental care and cleaning agent, based on the total weight thereof, comprises 2.0 to 19 wt. %, especially 4.0 to 17 wt. %, preferably 5.0 to 15 wt. %, more preferably 6.0 to 13 wt. %, still more preferably 7.0 to 12 wt. %, and in particular 8.0 to 11 wt. % of at least one aqueous dispersion of at least one phosphate-containing and/or phosphonate-containing polyurethane polymer. Use of the above-described amounts of the at least one aqueous dispersion of the at least one phosphate-containing and/or phosphonate-containing polyurethane polymer in the oral and dental care and cleaning agents according to the invention reduces the restaining of teeth to a particularly high degree. Moreover, these amounts do not cause incompatibilities with further ingredients, resulting in a long shelf life of these agents.

The oral and dental care and cleaning agents according to the invention comprise at least one anionic surfactant in an amount of 0.5 to 40 wt. % as a second essential ingredient b).

The at least one anionic surfactant is advantageously used in certain quantity ranges. Preferred oral and dental care and cleaning agents according to the invention are thus characterized by comprising, based on the total weight thereof, 0.5 to 30 wt. %, especially 0.5 to 20 wt. %, preferably 0.75 to 10 wt. %, more preferably 0.9 to 5.0 wt. %, and in particular 1.0 to 2.0 wt. % anionic surfactant(s). If a mixture of different anionic surfactants is used, the above-described quantity information refers to the mixture of these surfactants. The use of anionic surfactants in the above-described quantity ranges increases the adhesion of the phosphate-containing and/or phosphonate-containing polyurethane polymer, so that the restaining of teeth can be further reduced in this way. Moreover, these amounts ensure sufficient foaming and an adequate cleaning performance, so that the substances resulting in restaining can be efficiently dispersed and removed.

Typical examples of anionic surfactants are soaps, alkylbenzene sulfonates, alkane sulfonates, olefin sulfonates, alkyl ether sulfonates, glycerol ether sulfonates, α-methyl ester sulfonates, sulfo fatty acids, alkyl sulfates, fatty alcohol ether sulfates, glycerol ether sulfates, hydroxy mixed ether sulfates, monoglyceride (ether) sulfates, fatty acid amide (ether) sulfates, monoalkyl and dialkyl sulfosuccinates, monoalkyl and dialkyl sulfosuccinamate, sulfotriglycerides, amide soaps, ether carboxylic acids and the salts thereof, fatty acid isethionates, fatty acid sarcosinates, fatty acid taurides, N-acyl amino acids such as acyl lactylate, acyl tartrate, acyl glutamate and acyl aspartate, alkyloligoglucoside sulfates, protein fatty acid condensates (in particular wheat-based vegetable products) and alkyl (ether) phosphates. If the anionic surfactants include polyglycol ether chains, these can have a conventional, but preferably a narrow distribution of homologs.

The use of certain anionic surfactants has proven to be preferred within the scope of the present invention. It is thus advantageous according to the present invention if the oral and dental care and cleaning agent, based on the total weight thereof, comprises 0.5 to 30 wt. %, especially 0.5 to 20 wt. %, more preferably 0.75 to 10 wt. %, still more preferably 0.9 to 5.0 wt. %, and in particular 1.0 to 2.0 wt. % sodium dodecyl sulfate. Using such alkyl sulfates allows the adhesion of the phosphate-containing and/or phosphonate-containing polyurethane polymer on the tooth enamel to be further increased. Moreover, the combination of this polyurethan polymer with the special alkyl sulfates results in an improved foam quality, foam stability, and foam quantity, creating in a more pleasant product feel and improved cleaning performance.

The agents according to the invention preferably comprise one or more abrasives, preferably from the group of the precipitated silicas. The precipitated silicas, which preferably have certain specific surface areas, are preferably used within certain quantity ranges, and in particular precipitated silicas having low specific surface areas according to ISO 5794-1, Appendix D, are preferably used. Preferred oral and dental care and cleaning agents according to the invention comprise 2.5 to 19.5 wt. %, especially 5 to 19 wt. %, particularly preferably 7.5 to 18.5 wt. %, more preferably 8.0 to 18 wt. %, and in particular 10.0 to 17.5 wt. % precipitated silica(s) having a specific surface area according to ISO 5794-1, Appendix D, of ≤60 m$^2$/g, especially of ≤52.5 m$^2$/g, more preferably of ≤49 m$^2$/g, and in particular of ≤47 m$^2$/g.

In further preferred agents according to the invention, the precipitated silicas used are characterized by further physical parameters. Precipitated silicas to be preferably used have tamped densities >360 g/l (measured according to ISO 787-11), particularly preferably >375 g/l, more preferably >400 g/l, and in particular >425 g/l.

It is further preferred to use precipitated silicas that have a DBP absorption according to DIN 53601 of less than 140 g/100 g. Precipitated silicas to be used especially particularly preferably according to the invention have a DBP absorption according to DIN 53601 of less than 135 g/100 g, preferably a DBP absorption according to DIN 53601 of less than 130 g/100 g, and in particular of less than 125 g/100 g.

Particularly preferred agents according to the invention comprise 2.5 to 25 wt. %, especially 5 to 20 wt. %, particularly preferably 7.5 to 17.5 wt. %, more preferably 8.0 to 15.0 wt. %, and in particular 10.0 to 14.0 wt. % precipitated silica(s) having a specific surface area according to ISO 5794-1, Appendix D, of ≤45 m$^2$/g, and a tamped density (measured according to ISO 787-11) of >425 g/l.

Further preferred agents according to the invention comprise 2.5 to 25 wt. %, especially 5 to 20 wt. %, particularly preferably 7.5 to 17.5 wt. %, more preferably 8.0 to 15.0 wt. %, and in particular 10.0 to 14.0 wt. % precipitated silica(s) having a specific surface area according to ISO 5794-1, Appendix D, of ≤45 m$^2$/g, and a DBP absorption according to DIN 53601 of less than 125 g/100 g.

In particular, preferred agents according to the invention comprise 2.5 to 25 wt. %, especially 5 to 20 wt. %, particularly preferably 7.5 to 17.5 wt. %, more preferably 8.0 to 15.0 wt. %, and in particular 10.0 to 14.0 wt. % precipitated silica(s) having a specific surface area according to ISO 5794-1, Appendix D, of ≤45 m$^2$/g, a tamped density (measured according to ISO 787-11) of >425 g/l, and a DBP absorption according to DIN 53601 of less than 125 g/100 g.

In addition to the aforementioned precipitated silicas a), the agents according to the invention can comprise further polishing agents. In principle, all friction bodies known for toothpastes are suitable polishing agents, in particular those that do not include any calcium ions. Preferred suitable polishing agent components may therefore be aluminum hydroxide, aluminum oxide, sodium aluminosilicates, organic polymers or mixtures of such friction bodies.

It is preferred for the compositions according to the invention to comprise little to no precipitated silicas that have a specific surface area according to ISO 5794-1, Appendix D, of >55 m$^2$/g. If these types of silicas are to be used, the weight ratio of precipitated silicas having a specific surface area according to ISO 5794-1, Appendix D, of ≤55 m$^2$/g (ingredient c)) to precipitated silicas having a specific surface area according to ISO 5794-1, Appendix D, of >55 m$^2$/g is especially >1:1, more preferably >2:1, still more preferably >5:1, particularly preferably >10:1, and in particular >50:1.

It is also possible, for example, for aluminum oxide in the form of weakly calcined alumina to be present in a quantity of approximately 1 to 5 wt. % as a further polishing agent component. Such a suitable aluminum oxide is available under the trade name "Poliertonerde P10 feinst (ultrafine polishing alumina P10)" (Giulini Chemie). Moreover all friction bodies known for toothpastes are suitable polishing agents, for example sodium aluminosilicates such as zeolite A, organic polymers such as polymethacrylate, or mixtures of these and the above-described friction bodies.

The cosmetic agents according to the invention can moreover comprise at least one fluoride, selected from the group consisting of (i) sodium fluoride; (ii) potassium fluoride; (iii) tin(II) fluoride; (iv) amine fluorides and (v) the mixtures thereof. In particular, the use of sodium fluoride has proven to be advantageous. Preferred agents according to the present invention are thus characterized by comprising, based on the total weight thereof, 0.1 to 0.8 wt. %, especially 0.1 to 0.7 wt. %, preferably 0.1 to 0.6 wt. %, preferably 0.1 to 0.5 wt. %, and in particular 0.1 to 0.3 wt. % sodium fluoride. The use of fluorides in the oral and dental cleaning agents according to the invention not only hardens the tooth enamel, but also effectively prevents tooth decay. In addition, the use of amine fluorides causes dentin tubes of exposed tooth necks to be closed, so that the use of the agents according to the invention can decrease the sensitivity toward hot, cold, sweet and sour foods.

The oral and dental care and cleaning products according to the invention can comprise further ingredients. The use of what are known as humectants is preferred, which prevent toothpastes from drying out. In what are known as liquid dentifrices having a flowable rheology, they serve as a matrix and are used in higher quantities. In mouthwashes and oral rinses, these alcohols are used as consistency regulators and additional sweeteners.

Preferred oral and dental care and cleaning agents according to the invention here are those that comprise, based on the weight thereof, 0.5 to 60 wt. %, especially 0.75 to 55 wt. %, particularly preferably 1 to 50 wt. %, and in particular 2 to 40 wt. % of at least one polyhydric alcohol from the group consisting of sorbitol and/or glycerol and/or 1,2-propylene glycol-% or the mixtures thereof.

For certain fields of application, it may be advantageous to use only one of the three ingredients described above. Sorbitol is preferred in the majority of cases. However, mixtures of two of the three substances, or of all three substances, may be preferred in other fields of application. A mixture of glycerol, sorbitol and 1,2-propylene glycol in a weight ratio of 1:(0.5-1):(0.1-0.5) has proven to be particularly advantageous.

In addition to sorbitol or glycerol or 1,2-propylene glycol, further suitable polyhydric alcohols are those that have at least 2 OH groups, preferably mannitol, xylitol, polyethylene glycol, polypropylene glycol and the mixtures thereof. Among these compounds, those having 2 to 12 OH groups, and in particular those having 2, 3, 4, 5, 6 or 10 OH groups are preferred.

For example, polyhydroxy compounds having 2 OH groups are glycol (CH$_2$(OH)CH$_2$OH) and other 1,2-diols such as H—(CH$_2$)$_n$—CH(OH)CH$_2$OH where n=2, 3, 4, 5, 6, 7, 8, 9, 10, 11, 12, 13, 14, 15, 16, 17, 18, 19, 20. According to the invention, it is also possible to use 1,3-diols such as H—(CH$_2$)$_n$—CH(OH)CH$_2$CH$_2$OH where n=1, 2, 3, 4, 5, 6, 7, 8, 9, 10, 11, 12, 13, 14, 15, 16, 17, 18, 19, 20. The (n,n+1)- or (n,n+2)-diols having non-terminal OH groups can likewise be used. Important representatives of polyhydroxy compounds having 2 OH groups are also the polyethylene and polypropylene glycols. Preferred further polyhydric alcohols that can be used are, for example, xylitol, propylene glycols, polyethylene glycols, in particular those having average molecular weights of 200 to 800.

The use of sorbitol is particularly preferred, so that products that, except for sorbitol, do not comprise any other polyhydric alcohols are particularly preferred.

The agents according to the invention may additionally include wound healing and anti-inflammatory substances, such as active ingredients against gingivitis. Such substances may be selected from allantoin, azulene, chamomile extracts, tocopherol, panthenol, bisabolol and sage extracts, for example.

Oral and dental care and cleaning agents may also include substances that are effective against plaque and/or tartar, for example.

Substances effective against tartar can be chelating agents, for example, such as ethylenediaminetetraacetic acid and the sodium salts thereof, pyrophosphate salts such as the water-soluble dialkali or tetraalkali metal pyrophosphate salts, for example Na$_4$P$_2$O$_7$, K$_4$P$_2$O$_7$, Na$_2$K$_2$P$_2$O$_7$, Na$_2$H$_2$P$_2$O$_7$ and K 2H2P207, or polyphosphate salts, which may be selected from water-soluble alkali metal tripolyphosphates such as sodium tripolyphosphate and potassium tripolyphosphate, for example. The phosphate-containing and/or phosphonate-containing polyurethane polymers used according to the invention are not covered by these active ingredients.

Preferred oral and dental care and cleaning agents according to the invention are characterized by additionally comprising phosphate(s), preferably alkali metal phosphate(s), and in particular sodium tripolyphosphate, preferably in quantities of 1 to 10 wt. %, particularly preferably 2 to 8 wt. %, and in particular 3 to 7 wt. %, in each case based on the total agent.

The consistency regulators (or binding agents) that are used are, for example, natural and/or synthetic water-soluble polymers such as alginates, carrageenates, tragacanth, starch and starch ether, cellulose ethers such as carboxymethylcellulose (Na salt), hydroxyethyl cellulose, methylhydroxypropylcellulose, guar, acacia gum, agar-agar, xanthan gum, succinoglycan gum, locust bean gum, pectins, water-soluble carboxyvinyl polymers (such as Carbopol® types), polyvinyl alcohol, polyvinylpyrrolidone, polyethylene glycols, in particular those having molecular weights of 1,500 to 1,000,000.

Further substances, which are suitable for viscosity control, are phyllosilicates, for example, such as montmorrillonite clays, colloidal thickening silicas, such as silica aerogels, fumed silicas or finely ground precipitated silicas. It is also possible to use viscosity-stabilizing additives from the group consisting of the cationic, zwitterionic or ampholytic nitrogenous surfactants, the hydroxypropyl-substituted hydrocolloids or the polyethylene glycol/polypropylene glycol copolymers having a mean molecular weight of 1,000 to 5,000, or a combination of the described compounds, in the toothpastes.

Xanthan gum has an especially particularly good compatibility with the combination according to the invention. Agents according to the invention that include xanthan gum have an extraordinary shelf life and have a pleasant product feel. Preferred oral and dental care and cleaning agents according to the invention are thus characterized by additionally comprising 0.1 to 7.5 wt. %, especially 0.25 to 5 wt. %, more preferably 0.5 to 2.5 wt. %, and in particular 0.6 to 1.5 wt. % xanthan gum.

In addition to the described mandatory components, the dental care agents according to the invention may include further auxiliary agents and additives which are known per se. One additive which has been long known as a toothpaste component is particularly effective in the dental care agents according to the invention: calcium glycerophosphate, the calcium salt of glycerol-1-phosphoric acid or of glycerol-2-phosphoric acid or of glycerol-3-phosporic acid, the mirror-image isomer of glycerol-1-phosphoric acid, or a mixture of these acids. This compound has a remineralizing effect in dental care products because it supplies both calcium ions and phosphate ions. Calcium glycerophosphate is preferably used in quantities of 0.01 to 1 wt. % in the dental care agents according to the invention. Overall, the dental care agents according to the invention may include typical auxiliary substances and additives in quantities of up to 10 wt. %.

The organoleptic properties of the dental care agents according to the invention can be improved, for example, by adding flavoring oils and sweeteners.

The flavoring oils can be any of the natural and synthetic flavors typically used for oral and dental care products. Natural flavoring agents may be present either in the form of the natural essential oils isolated from drugs or in the form of the individual components isolated therefrom.

Suitable sweeteners are, for example, saccharin sodium, sodium cyclamate, sucrose, lactose, maltose, and fructose.

Further typical auxiliary substances and additives for toothpastes and mouthwashes or oral rinse solutions are
- surface-active substances from the group consisting of zwitterionic, amphoteric, and non-ionic surfactants and the mixtures thereof;
- solvents and solubilizers, such as lower monohydric or polyhydric alcohols or ethers, such as ethanol, 1,2-propylene glycol, diethylene glycol or butyl diglycol;
- pigments, such as titanium dioxide;
- dyes;
- buffer substances, such as primary, secondary or tertiary alkali phosphates or citric acid/Na citrate;
- other wound healing or anti-inflammatory substances, such as allantoin, urea, azulene, active chamomile substances, acetylsalicylic acid derivatives or thiocyanate;
- further vitamins such as ascorbic acid, biotin, tocopherol or rutin;
- mineral salts such as manganese salts, zinc salts or magnesium salts.

Particularly preferred embodiments AF1 to AF20 of the oral and dental care and cleaning agents according to the invention are listed hereafter (all information in percent by weight, aqueous PuD=aqueous dispersion of at least one phosphate-containing and/or phosphonate-containing polyurethane polymer):

|  | AF1 | AF2 | AF3 | AF4 |
|---|---|---|---|---|
| Aqueous PuD | 2.0-19 | 5.0-15 | 7.0-12 | 8.0-11 |
| Anionic surfactant | 0.5-30 | 0.5-20 | 0.75-10 | 1.0-2.0 |
| Cosmetic carrier[1] | to make 100 | to make 100 | to make 100 | to make 100 |

|  | AF5 | AF6 | AF7 | AF8 |
|---|---|---|---|---|
| Aqueous PuD | 2.0-19 | 5.0-15 | 7.0-12 | 8.0-11 |
| Anionic surfactant | 0.5-30 | 0.5-20 | 0.75-10 | 1.0-2.0 |
| Sodium fluoride | 0.1-0.8 | 0.1-0.7 | 0.1-0.5 | 0.1-0.3 |
| Cosmetic carrier[1] | to make 100 | to make 100 | to make 100 | to make 100 |

|  | AF9 | AF10 | AF11 | AF12 |
|---|---|---|---|---|
| Aqueous PuD | 2.0-19 | 5.0-15 | 7.0-12 | 8.0-11 |
| Anionic surfactant[2] | 0.5-30 | 0.5-20 | 0.75-10 | 1.0-2.0 |
| Sodium fluoride | 0.1-0.8 | 0.1-0.7 | 0.1-0.5 | 0.1-0.3 |
| Cosmetic carrier[1] | to make 100 | to make 100 | to make 100 | to make 100 |

|  | AF13 | AF14 | AF15 | AF16 |
|---|---|---|---|---|
| Aqueous PuD | 2.0-19 | 5.0-15 | 7.0-12 | 8.0-11 |
| Anionic surfactant[2] | 0.5-30 | 0.5-20 | 0.75-10 | 1.0-2.0 |
| $C_8$-$C_{20}$ alkyl betaine | 0.1-4.0 | 0.1-3.0 | 0.1-2.0 | 0.1-1.0 |
| Cosmetic carrier[1] | to make 100 | to make 100 | to make 100 | to make 100 |

|  | AF17 | AF18 | AF19 | AF20 |
|---|---|---|---|---|
| Aqueous PuD | 2.0-19 | 5.0-15 | 7.0-12 | 8.0-11 |
| Anionic surfactant 2) | 0.5-30 | 0.5-20 | 0.75-10 | 1.0-2.0 |
| Sodium fluoride | 0.1-0.8 | 0.1-0.7 | 0.1-0.5 | 0.1-0.3 |
| $C_8$-$C_{20}$ alkyl betaine | 0.1-4.0 | 0.1-3.0 | 0.1-2.0 | 0.1-1.0 |
| Cosmetic carrier[1] | to make 100 | to make 100 | to make 100 | to make 100 |

[1] water,
[2] sodium dodecyl sulfate.

For each above-described, particularly preferred embodiment AF1 to AF20, the PuD1 to PuD12 indicated in the table below is used as the aqueous PuD. All quantity information is provided in wt. % and refers to the total weight of the corresponding polyurethane polymer.

| No. | Components of the phosphate-containing and/or phosphonate-containing polyurethane polymer |
|---|---|
| PuD1 | Polyurethane compound formula (I) & ionic polyether compound formula (II) & non-ionic polyether compound formula (III) & phosphonate-containing compound formula (IVa) |

| No. | Components of the phosphate-containing and/or phosphonate-containing polyurethane polymer |
|---|---|
| PuD2 | Polyurethane compound formula (I) & ionic polyether compound formula (IIa) & non-ionic polyether compound formula (IIIa) & phosphonate-containing compound formula (IVa-1), phosphate content 0.1 to 1.0 wt. % |
| PuD3 | Polyurethane compound formula (I) & ionic polyether compound formula (IIa) + non-ionic polyether compound formula (IIIa) in a weight ratio of 2:1 to 1:2 & phosphonate-containing compound formula (IVa-1), phosphate content 0.1 to 1.0 wt. % |
| PuD4 | Polyurethane compound formula (I) & ionic polyether compound formula (IIa) + two non-ionic polyether compounds, each of formula (IIIa) and of different number average molecular weights $M_n$, in a weight ratio of 1:1 & phosphonate-containing compound formula (IVa-1), phosphate content 0.1 to 1.0 wt. % |
| PuD5 | Polyurethane compound formula (I) & ionic polyether compound formula (IIa) + two non-ionic polyether compounds, each of formula (IIIa) and of different number average molecular weights $M_n$, in a weight ratio of 1:1 & phosphonate-containing compound formula (IVa-1) & polyester compound in the form of the condensate of adipic acid with butylene glycol and/or the condensate of azelaic acid with 1,6-hexanediol, phosphate content 0.1 to 0.1 to 1.0 wt. % |
| PuD6 | Polyurethane compound formula (I) & 3.5 to 4.5 wt. % ionic polyether compound formula (IIa) + 7.5 to 9.5 wt. % of two non-ionic polyether compounds, each of formula (IIIa) and of different number average molecular weights $M_n$, in a weight ratio of 1:1 & phosphonate-containing compound formula (IVa-1) & 70 to 80 wt. % polyester compound in the form of the condensate of adipic acid with butylene glycol and/or the condensate of azelaic acid with 1,6-hexanediol, phosphate content 0.1 to 0.1 to 1.0 wt. % |
| PuD7 | Polyurethane compound formula (I) & ionic polyether compound formula (II) & non-ionic polyether compound formula (III) & phosphonate-containing compound formula (IVb) |
| PuD8 | Polyurethane compound formula (I) & ionic polyether compound formula (IIa) & non-ionic polyether compound formula (IIIa) & phosphonate-containing compound formula (IVb-1), phosphate content 0.1 to 1.0 wt. % |
| PuD9 | Polyurethane compound formula (I) & ionic polyether compound formula (IIa) + non-ionic polyether compound formula (IIIa) in a weight ratio of 2:1 to 1:2 & phosphonate-containing compound formula (IVb-1), phosphate content 0.1 to 1.0 wt. % |
| PuD10 | Polyurethane compound formula (I) & ionic polyether compound formula (IIa) + two non-ionic polyether compounds, each of formula (IIIa) and of different number average molecular weights $M_n$, in a weight ratio of 1:1 & phosphonate-containing compound formula (IVb-1), phosphate content 0.1 to 1.0 wt. % |
| PuD11 | Polyurethane compound formula (I) & ionic polyether compound formula (IIa) + two non-ionic polyether compounds, each of formula (IIIa) and of different number average molecular weights $M_n$, in a weight ratio of 1:1 & phosphonate-containing compound formula (IVb-1) & polyester compound in the form of the condensate of adipic acid with butylene glycol and/or the condensate of azelaic acid with 1,6-hexanediol, phosphate content 0.1 to 0.1 to 1.0 wt. % |
| PuD12 | Polyurethane compound formula (I) & 3.5 to 4.5 wt. % ionic polyether compound formula (IIa) + 7.5 to 9.5 wt. % of two non-ionic polyether compounds, each of formula (IIIa) and of different number average molecular weights $M_n$, in a weight ratio of 1:1 & phosphonate-containing compound formula (IVb-1) & 70 to 80 wt. % polyester compound in the form of the condensate of adipic acid with butylene glycol and/or the condensate of azelaic acid with 1,6-hexanediol, phosphate content 0.1 to 0.1 to 1.0 wt. % |

All above-described PuD1 to PuD12 preferably have a volume median particle size D50 of 150 to 400 nm (measured by way of dynamic light scattering (DLS)).

The above-described particularly preferred embodiments of the agents according to the invention result in a high decrease or in a prevention of restaining of teeth from bacterial impurities and foodstuffs. In addition, these yield an outstanding shelf life. These also result in a high foam quality, foam quantity and foam stability, allowing excellent cleaning of the teeth and the oral cavity.

Agents according to the invention can be formulated as toothpastes or cream dentifrices. If electric toothbrushes are used, the agents according to the invention have the further advantage that these are already effective in small amounts, and moreover do not impair the mechanics of the electric brush head. A further subject matter of the present invention is thus a method for cleaning teeth, characterized by the following steps:

a) providing a toothbrush, the brush head of which can optionally be set in motion electrically;

b) applying 0.5 to 5 g of an agent according to the invention to the brush head;

c) brushing the teeth with the agent disclosed herein for 30 to 300 seconds using the brush head, which optionally can be set in motion electrically.

What was said with respect to the agents according to the invention applies, mutatis mutandis, with respect to preferred embodiments of the method according to the invention.

Finally, a further subject matter of the present invention is the use of oral and dental care and cleaning agents, comprising, based on the weight thereof, a) 1 to 20 wt. % of an aqueous dispersion of at least one phosphate-containing and/or phosphonate-containing polyurethane polymer, and b) 0.5 to 40 wt. % anionic surfactant(s)

to reduce the restaining of teeth and/or to reduce biofilm development on dental surfaces and/or to reduce the adhesion of bacteria to dental surfaces and/or to extend the antibacterial action of antibacterial substances.

What was said with respect to the agents according to the invention and with respect to the method according to the invention applies, mutatis mutandis, with respect to preferred embodiments of the use according to the invention.

In summary, the present invention is in particular characterized by the following items:

1. An oral and dental care and cleaning agent, comprising, based on the total weight thereof,
   a) 1 to 20 wt. % of an aqueous dispersion of at least one phosphate-containing and/or phosphonate-containing polyurethane polymer, and
   b) 0.5 to 40 wt. % anionic surfactant(s).

2. The oral and dental care and cleaning agent according to item 1, characterized in that the at least one phosphate-containing and/or phosphonate-containing polyurethane polymer comprises at least one polyurethane compound of formula (I), and at least one ionic polyether compound of formula (II), and at least one non-ionic polyether compound of formula (III), and at least one phosphate-containing and/or phosphonate-containing compound of formula (IVa) and/or (IVb) and/or (IVc)

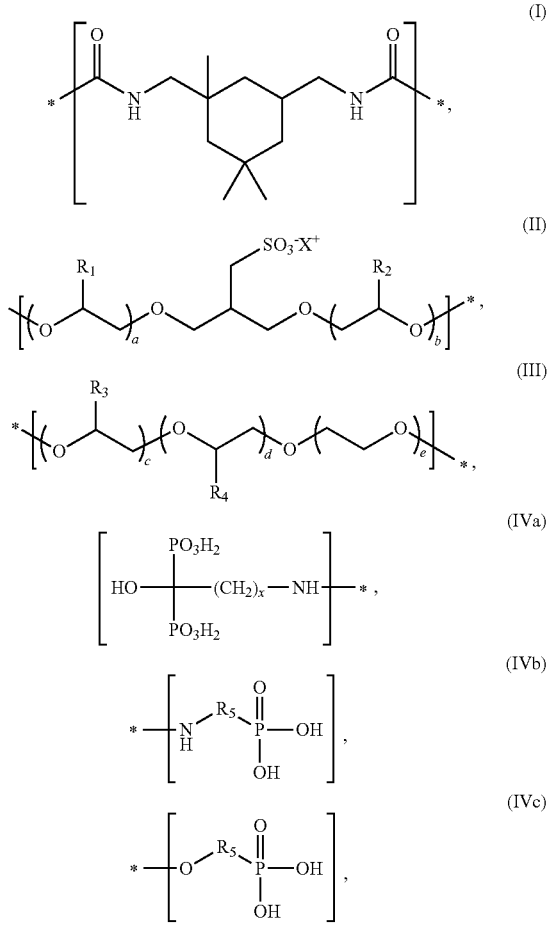

where
$R_1$ and $R_2$, each independently of one another, denote a linear or branched $C_1$ to $C_4$ alkyl group, in particular a linear $C_1$ to $C_2$ alkyl group; a and b, each independently of one another, denote integers from 1 to 6, in particular from 1 to 4; $X^+$ denotes a physiologically compatible cation, in particular sodium;

$R_3$ and $R_4$, each independently of one another, denote hydrogen or a linear or branched $C_1$ to $C_4$ alkyl group, in particular hydrogen or a linear $C_1$ to $C_2$ alkyl group, wherein at least one of the groups $R_3$ or $R_4$ denotes a linear or branched $C_1$ to $C_4$ alkyl group; e denotes integers from 1 to 15, preferably from 1 to 7; and c and d, each independently of one another, denote integers from 10 to 60, preferably from 20 to 40;

x denotes integers from 1 to 10, preferably from 2 to 8; and $R_5$ denotes a respective linear or branched $C_1$ to $C_4$ alkyl group, in particular a linear $C_1$ to $C_2$ alkyl group.

3. The oral and dental care and cleaning agent according to item 2, characterized in that the at least one phosphate-containing and/or phosphonate-containing polyurethane polymer comprises at least one ionic polyether compound of formula (IIa)

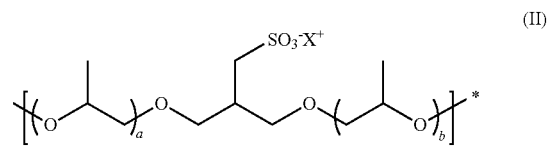

where
a and b, each independently of one another, denote integers from 1 to 4, and $X^+$ denotes sodium.

4. The oral and dental care and cleaning agent according to either item 2 or 3, characterized in that the at least one phosphate-containing and/or phosphonate-containing polyurethane polymer comprises at least one non-ionic polyether compound of formula (IIIa)

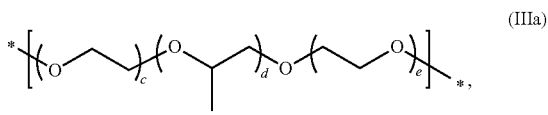

where
c and e, each independently of one another, denote integers from 1 to 7; and d denotes integers from 20 to 40.

5. The oral and dental care and cleaning agent according to any one of items 2 to 4, characterized in that the at least one non-ionic polyether compound of formula (III), and in particular of formula (IIIa), has a number average molecular weight $M_n$ of 500 to 5,000 g/mol, especially of 800 to 4,000/gmol, preferably of 1,000 to 3,000 g/mol, and in particular of 1,800 to 2,200 g/mol.

6. The oral and dental care and cleaning agent according to any one of items 2 to 5, characterized in that the at least one phosphate-containing and/or phosphonate-containing polyurethane polymer comprises at least two non-ionic polyether compounds, each of formula (III), and in particular (IIIa), and of number average molecular weights $M_n$ that are different from one another, in a weight ratio of 1:1.

7. The oral and dental care and cleaning agent according to any one of items 2 to 6, characterized in that the at least one phosphonate-containing polyurethane polymer comprises at least one phosphonate-containing compound of formula (IVa-1) and/or (IVb-1) and/or (IVc-1)

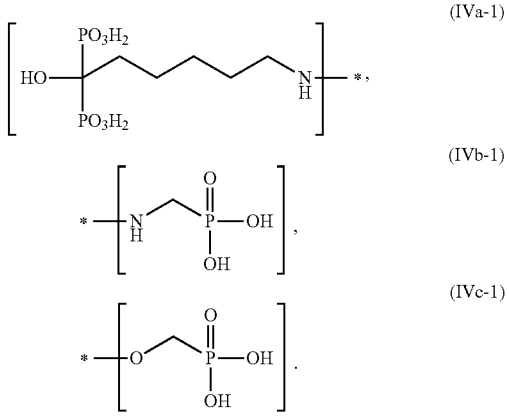

8. The oral and dental care and cleaning agent according to any one of items 2 to 7, characterized in that the at least one phosphate-containing and/or phosphonate-containing polyurethane polymer comprises the at least one polyurethane compound of formula (I), based on the total weight thereof, in a total amount of 4.0 to 30 wt. %, especially of 5.0 to 25 wt. %, preferably of 8.0 to 20 wt. %, and in particular of 10 to 15 wt. %.

9. The oral and dental care and cleaning agent according to any one of items 2 to 8, characterized in that the at least one phosphate-containing and/or phosphonate-containing polyurethane polymer has a weight ratio of the at least one ionic polyether compound of formula (II), and in particular of formula (IIa), to the at least one non-ionic polyether compound of formula (III), and in particular of formula (IIIa), of 2:1 to 1:5, especially of 2:1 to 1:3, and in particular of 2:1 to 1:2.

10. The oral and dental care and cleaning agent according to any one of items 2 to 9, characterized in that the at least one phosphate-containing and/or phosphonate-containing polyurethane polymer comprises the at least one ionic polyester compound of formula (II), in particular of formula (IIa), based on the total weight thereof, in a total amount of 2.0 to 7.0 wt. %, especially of 2.5 to 6.0 wt. %, preferably of 3.0 to 5.0 wt. %, and in particular of 3.5 to 4.5 wt. %.

11. The oral and dental care and cleaning agent according to any one of items 2 to 10, characterized in that the at least one phosphate-containing and/or phosphonate-containing polyurethane polymer comprises the at least one non-ionic polyester compound of formula (III), in particular of formula (IIIa), based on the total weight thereof, in a total amount of 4.0 to 20 wt. %, especially of 5.0 to 15 wt. %, preferably of 6.0 to 12 wt. %, and in particular of 7.5 to 9.5 wt. %.

12. The oral and dental care and cleaning agent according to any one of items 2 to 11, characterized in that the at least one phosphate-containing and/or phosphonate-containing polyurethane polymer additionally comprises at least one polyester compound, selected from condensates of adipic acid with butylene glycol, condensates of azelaic acid with 1,6-hexanediol, and the mixtures thereof.

13. The oral and dental care and cleaning agent according to item 12, characterized in that the at least one polyether compound has a number average molecular weight $M_n$ of 1,200 to 5,500 g/mol, especially of 1,500 to 5,000/gmol, preferably of 1,800 to 4,500 g/mol, and in particular of 2,000 to 4,000 g/mol.

14. The oral and dental care and cleaning agent according to either item 12 or 13, characterized in that the at least one phosphate-containing and/or phosphonate-containing polyurethane polymer comprises the at least one polyester compound, based on the total weight thereof, in a total amount of 55 to 87 wt. %, especially of 60 to 85 wt. %, preferably of 65 to 82 wt. %, and in particular of 70 to 80 wt. %.

15. The oral and dental care and cleaning agent according to any one of items 2 to 14, characterized in that the phosphate-containing and/or phosphonate-containing polyurethane polymer has a phosphate content, based on the total weight thereof, of 0.005 to 3.0 wt. %, especially of 0.01 to 2.5 wt. %, preferably of 0.05 to 2.0 wt. %, and in particular of 0.1 to 1.0 wt. %.

16. The oral and dental care and cleaning agent according to any one of the preceding items, characterized in that the aqueous dispersion has a volume median particle size D50 of 50 to 500 nm, especially of 80 to 400 nm, preferably of 100 to 400 nm, and in particular 150 to 400 nm.

17. The oral and dental care and cleaning agent according to any one of the preceding items, characterized in that the aqueous dispersion has a solids content, based on the total weight of the dispersion, of 10 to 60 wt. %, especially of 10 to 55 wt. %, preferably of 10 to 52 wt. %, and in particular of 10 to 50 wt. %.

18. The oral and dental care and cleaning agent according to any one of the preceding items, characterized in that the aqueous dispersion does not comprise any phosphate-containing and/or phosphonate-containing compound(s), and in particular phosphate-containing and/or phosphonate-containing compound(s) of formula(s) (IVa) to (IVc), and (IVa-1) to (IVc-1).

19. The oral and dental care and cleaning agent according to any one of the preceding items, characterized by comprising, based on the total weight thereof, 2.0 to 19 wt. %, especially 4.0 to 17 wt. %, preferably 5.0 to 15 wt. %, more preferably 6.0 to 13 wt. %, still more preferably 7.0 to 12 wt. %, and in particular 8.0 to 11 wt. % of at least one aqueous dispersion of at least one phosphate-containing and/or phosphonate-containing polyurethane polymer.

20. The oral and dental care and cleaning agent according to any one of the preceding items, characterized by comprising, based on the total weight thereof, 0.5 to 30 wt. %, especially 0.5 to 20 wt. %, preferably 0.75 to 10 wt. %, more preferably 0.9 to 5.0 wt. %, and in particular 1.0 to 2.0 wt. % anionic surfactant(s).

21. The oral and dental care and cleaning agent according to any one of the preceding items, characterized by comprising, based on the total weight thereof, 0.5 to 30 wt. %, especially 0.5 to 20 wt. %, more preferably 0.75 to 10 wt. %, still more preferably 0.9 to 5.0 wt. %, and in particular 1.0 to 2.0 wt. % sodium dodecyl sulfate.

22. The oral and dental care and cleaning agent according to any one of the preceding items, characterized by comprising, based on the total weight thereof, 2.5 to 19.5 wt. %, especially 5 to 19 wt. %, preferably 7.5 to 18.5 wt. %, more preferably 8.0 to 18 wt. %, and in particular 10.0 to 17.5 wt. % precipitated silica(s) having a specific surface area according to ISO 5794-1, Appendix D, of $\leq 60$ m$^2$/g, especially of $\leq 52.5$ m$^2$/g, preferably of $\leq 49$ m$^2$/g, and in particular of $\leq 47$ m$^2$/g.

23. The oral and dental care and cleaning agent according to any one of the preceding items, characterized by comprising, based on the total weight thereof, 0.1 to 0.8 wt. %, in particular 0.1 to 0.7 wt. %, especially 0.1 to 0.6 wt. %, preferably 0.1 to 0.5 wt. %, and in particular 0.1 to 0.3 wt. % sodium fluoride.

24. A method for cleaning teeth, characterized by the following steps:
   a) providing a toothbrush, the brush head of which can optionally be set in motion electrically;
   b) applying 0.5 to 5 g of an agent according to any one of items 1 to 23 to the brush head;
   c) brushing the teeth with the agent according to any one of items 1 to 30 for 30 to 300 seconds using the brush head, which optionally can be set in motion electrically.

25. Use of oral and dental care and cleaning agents, comprising, based on the weight thereof,
   a) 1 to 20 wt. % of an aqueous dispersion of at least one phosphate-containing and/or phosphonate-containing polyurethane polymer, and
   b) 0.5 to 40 wt. % anionic surfactant(s)
to reduce the restaining of teeth and/or to reduce biofilm development on dental surfaces and/or to reduce the adhesion of bacteria to dental surfaces and/or to extend the antibacterial action of antibacterial substances.

The following examples describe the present invention in more detail, without limiting it to these examples.

EXAMPLES

1. Production of the Aqueous Dispersion of the at Least One Phosphate-Containing and/or Phosphonate-Containing Polyurethane Polymer 1.1 Aqueous Dispersion of Phosphonate-Containing Polyurethane PPuD-1 and PPuD-2

8.00 g of an ionic polyether polyol having a number average molecular weight $M_n$ of 425 g/mol (corresponds to ionic polyol compound of (IIa)), 8.00 g of a non-ionic polyether polyol having a number average molecular weight $M_n$ of 1,900 g/mol (corresponds to non-ionic polyol compound of formula (IIIa)), 8.00 g of a non-ionic polyether polyol having a number average molecular weight $M_n$ of 2,100 g/mol (corresponds to non-ionic polyol compound of formula (IIIa)), and 150 g of a polyether polyol having a number average molecular weight $M_n$ of 2,900 g/mol (corresponds to above-described polyester compound) were melted at 80° C. and dehydrated for 1.5 hours under vacuum (p<0.1 mbar). The piston was flooded with nitrogen, and isophorone diisocyanate (26.3 g) and a catalyst (Fomrez UL-28, 0.01 g; 0.020 g) were added at 70° C., and the reaction was carried out at 80° C. after initially raising the temperature. The NCO content was determined every half hour by way of back titration according to ISO 11909:2007-05. After the theoretical value of 1.68% had been reached (2 hours), 200 g dry acetone was added, and the mixture was cooled to 40° C. 200 g of this solution was placed in 300 g water at 40° C. and stirred for 5 minutes (Ultra Turrax, IKA T25; 11,000 rpm). The pre-emulsion was sent 4 times through a homogenizer (Microfluidics Corp. 110Y/2007094, comprising two chambers measuring 400 and 200 μm in diameter, respectively; working pressure 6 bar) at 40° C.

5.54 g (6-amino-1-hydroxyhexane-1,1-diyl)bis(phosphonic acid) (corresponds to phosphonate-containing compound of formula (IVa-1)) was added to 50 g of this aqueous dispersion of the NCO-terminated polyurethane polymer, the pH value was set to 12, and the mixture was stirred for 30 minutes at room temperature. A dialysis was subsequently carried out to separate the unbound phosphonate compound. For this purpose, a dialysis membrane made of cellulose ester having a molecular weight cut-off (MWCO) of 30,000 Da (Carl Roth GmbH & Co. KG, Germany) was used. The dialysis was carried out against distilled water (4,0000 g) with a decreasing salt concentration for 1 week. The aqueous phosphonate-containing polyurethane dispersion PPuD-1 thus obtained has a volume average particle diameter D50 of 233 nm (measured by way of DLS with a solids content of 0.01 wt. %, based on the total weight of the dispersion) and a phosphate content of 0.47 wt. %, based on the total weight of the polyurethane polymer (measured by way of ICP-OES on a freeze-dried sample).

Alternatively, 2.22 g aminomethylphosphonic acid (corresponds to phosphonate-containing compound of formula (IVb-1)) was added to 50 g of the aqueous dispersion of the NCO-terminated polyurethane polymer, and the remaining procedure was the same as described above, except that the pH value was set to 11. The aqueous phosphonate-containing polyurethane dispersion PPuD-2 thus obtained has a volume average particle diameter D50 of 174 nm (measured by way of DLS with a solids content of 0.01 wt. %, based on the total weight of the dispersion) and a phosphate content of 0.13 wt. %, based on the total weight of the polyurethane polymer (measured by way of ICP-OES on a freeze-dried sample).

2. Formulations (All Information in wt. %):

Example 1 Toothpaste Formulation

| | A | B | C | D | E | F |
|---|---|---|---|---|---|---|
| Sorbitol, 70% | 45 | 50 | 55 | 60 | 65 | 70 |
| Aqueous PuD[1)] | 8.0 | 10 | 8.5 | 9.0 | 9.5 | 11 |
| Anionic surfactant[2)] | 1.2 | 1.5 | 1.1 | 1.2 | 1.2 | 1.2 |
| Hydrated silica** | 20 | 18 | 17 | 15 | 12.5 | 15 |
| Sodium fluoride | 0.32 | 0.32 | 0.32 | 0.32 | 0.32 | 0.32 |
| Sodium saccharin | 0.25 | 0.25 | 0.25 | 0.25 | 0.25 | 0.25 |
| Tego Betain ZF | 0.60 | — | — | 0.60 | 0.60 | — |
| Flavoring agent | 0.1 | 0.1 | 0.1 | 0.1 | 0.1 | 0.1 |
| Water | | | to make 100 | | | |

[1)] preferably one of the above-described PuD1 to PuD12 or the aqueous dispersions PPuD-1 and PPuD-2 produced in item 1
[2)] preferably sodium dodecyl sulfate Example 2 Mouthwash Formulation

| | A | B | C | D | E | F |
|---|---|---|---|---|---|---|
| Sorbitol, 70% | 1 | 1.5 | 2 | 2.5 | 3 | 5 |
| Aqueous PuD[1)] | 8.0 | 10 | 8.5 | 9.0 | 9.5 | 11 |
| Anionic surfactant 2) | 1.2 | 1.5 | 1.1 | 1.2 | 1.2 | 1.2 |
| Hydrated silica** | 1 | 1.5 | 2 | 2.5 | 1 | 1 |
| Sodium fluoride | 0.11 | 0.11 | 0.11 | 0.11 | 0.11 | 0.11 |
| Sodium saccharin | 0.03 | 0.05 | 0.1 | 0.05 | 0.05 | 0.1 |
| PEG-60 Hydrogenated Castor Oil | 0.2 | 0.2 | 0.2 | 0.2 | 0.2 | 0.2 |
| Trisodium citrate dihydrate | 0.1 | 0.2 | 0.3 | 0.2 | 0.1 | 0.1 |
| Citric acid | 0.001 | 0.002 | 0.1 | 0.2 | 0.01 | 0.01 |
| Flavoring agent | 0.1 | 0.1 | 0.1 | 0.1 | 0.1 | 0.1 |
| Water | | | to make 100 | | | |

[1)] preferably one of the above-described PuD1 to PuD12 or the aqueous dispersions PPuD-1 and PPuD-2 produced in item 1
2) preferably sodium dodecyl sulfate While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An oral and dental care and cleaning agent, comprising, based on the total weight thereof,
   a) 1 to 20 wt. % of an aqueous dispersion of at least one phosphate-containing and/or phosphonate-containing polyurethane polymer, and
   0.5 to 40 wt. % anionic surfactant(s), wherein the at least one phosphate-containing and/or phosphonate-containing polyurethane polymer comprises at least one polyurethane compound of formula (I), and at least one ionic polyether compound of formula (II), and at least one non-ionic polyether compound of formula (III), and at least one phosphate-containing and/or phosphonate-containing compound of formula (IVa) and/or (IVb) and/or (IVc)

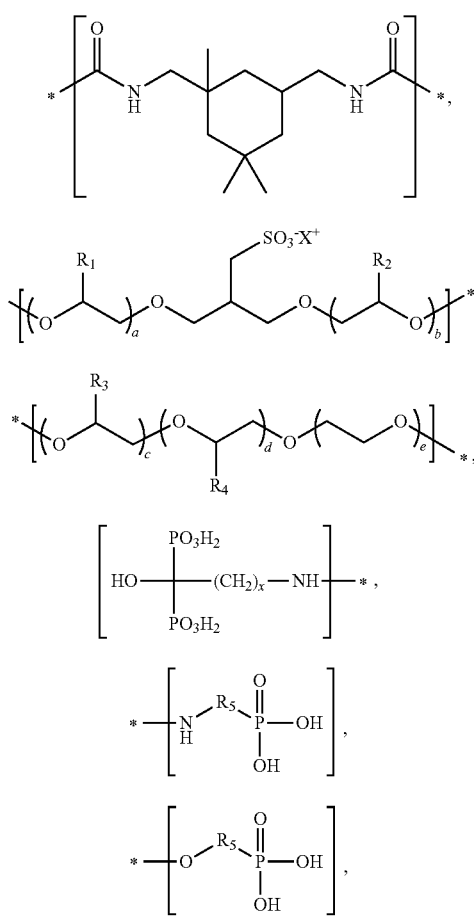

where
$R_1$ and $R_2$, each independently of one another, denote a linear or branched $C_1$ to $C_4$ alkyl group; a and b, each independently of one another, denote integers from 1 to 6;

$X^+$ denotes a physiologically compatible cation;

$R_3$ and $R_4$, each independently of one another, denote hydrogen or a linear or branched $C_1$ to $C_4$ alkyl group, wherein at least one of the groups $R_3$ or $R_4$ denotes a linear or branched $C_1$ to $C_4$ alkyl group; e denotes integers from 1 to 15; and c and d, each independently of one another, denote integers from 10 to 60;

x denotes integers from 1 to 10; and $R_5$ denotes a respective linear or branched $C_1$ to $C_4$ alkyl group.

2. The oral and dental care and cleaning agent according to claim 1, wherein the at least one phosphate-containing and/or phosphonate-containing polyurethane polymer comprises at least one phosphonate-containing compound of formula (IVa-1) and/or (IVb-1) and/or (IVc-1)

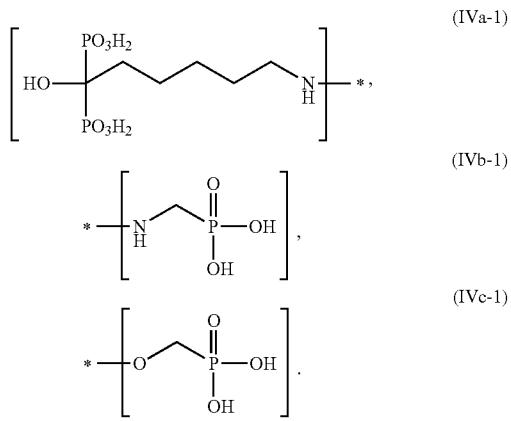

3. The oral and dental care and cleaning agent according to claim 1, wherein the at least one phosphate-containing and/or phosphonate-containing polyurethane polymer has a weight ratio of the at least one ionic polyether compound of formula (II), to the at least one non-ionic polyether compound of formula (III), of 2:1 to 1:5.

4. The oral and dental care and cleaning agent according to claim 3, wherein the weight ratio of the at least one ionic polyether compound of formula (II), to the at least one non-ionic polyether compound of formula (III) is 2:1 to 1:3.

5. The oral and dental care and cleaning agent according to claim 1, wherein the at least one phosphate-containing and/or phosphonate-containing polyurethane polymer includes at least one ionic polyether compound of formula (IIa)

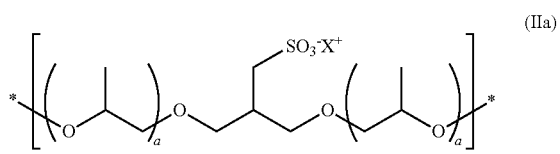

and to the at least one non-ionic polyether compound of formula (IIIa)

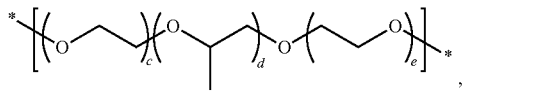
(IIIa)

and has a weight ratio of the at least one ionic polyether compound of formula (IIa), to the at least one non-ionic polyether compound of formula (IIIa) of 2:1 to 1:5.

6. The oral and dental care and cleaning agent according to claim 5, wherein the weight ratio of the at least one ionic polyether compound of formula (IIa) to the at least one non-ionic polyether compound of formula (IIIa) is 2:1 to 1:2.

7. The oral and dental care and cleaning agent according to claim 1, wherein the at least one phosphate-containing and/or phosphonate-containing polyurethane polymer additionally comprises at least one polyester compound, selected from the group consisting of: condensates of adipic acid with butylene glycol, condensates of azelaic acid with 1,6-hexanediol, and the mixtures thereof.

8. The oral and dental care and cleaning agent according claim 1, wherein in that the phosphate-containing and/or phosphonate-containing polyurethane polymer has a phosphate content, based on the total weight thereof, of 0.005 to 3.0 wt. %.

9. The oral and dental care and cleaning agent according claim 1, wherein in that the phosphate-containing and/or phosphonate-containing polyurethane polymer has a phosphate content, based on the total weight thereof, of 0.01 to 2.5 wt. %.

10. The oral and dental care and cleaning agent according claim 1, wherein in that the phosphate-containing and/or phosphonate-containing polyurethane polymer has a phosphate content, based on the total weight thereof, of 0.05 to 2.0 wt. %.

11. The oral and dental care and cleaning agent according claim 1, wherein in that the phosphate-containing and/or phosphonate-containing polyurethane polymer has a phosphate content, based on the total weight thereof, of 0.1 to 1.0 wt. %.

12. The oral and dental care and cleaning agent according claim 1, wherein the at least one aqueous dispersion of at least one phosphate-containing and/or phosphonate-containing polyurethane polymer comprises 5.0 to 15 wt. % based on the total weight thereof of the cleaning agent.

13. The oral and dental care and cleaning agent according claim 1, wherein the at least one aqueous dispersion of at least one phosphate-containing and/or phosphonate-containing polyurethane polymer comprises 8.0 to 11 wt. % based on the total weight thereof of the cleaning agent.

14. The oral and dental care and cleaning agent according to claim 1, wherein the anionic surfactant(s) comprise 0.5 to 30 wt. % of the total weight thereof.

15. The oral and dental care and cleaning agent according to claim 1, wherein the anionic surfactant(s) comprise 0.5 to 20 wt. % of the total weight thereof.

16. The oral and dental care and cleaning agent according to claim 1, wherein the anionic surfactant(s) comprise 0.75 to 10 wt. % of the total weight thereof.

17. The oral and dental care and cleaning agent according to claim 1, wherein the anionic surfactant(s) comprise 0.9 to 5.0 wt. % of the total weight thereof.

18. The oral and dental care and cleaning agent according to claim 1, wherein the anionic surfactant(s) comprise 1.0 to 2.0 wt. % of the total weight thereof.

19. A method for cleaning teeth, characterized by the following steps:
a) providing a toothbrush, the brush head of which can optionally be set in motion electrically;
b) applying 0.5 to 5 g of an agent according to claim 1 to the brush head;
c) brushing the teeth with the agent for 30 to 300 seconds using the brush head, which optionally can be set in motion electrically.

* * * * *